United States Patent
Mitomo et al.

(10) Patent No.: US 6,786,911 B2
(45) Date of Patent: Sep. 7, 2004

(54) STORAGE CASE HAVING SOFT INTRAOCULAR LENS FOLDING FUNCTION

(75) Inventors: Kikuo Mitomo, Tokyo (JP); Tomomitsu Tatsuishi, Tokyo (JP)

(73) Assignee: Hoya Healthcare Corporation, Tokyo (JP)

( * ) Notice: Subject to any disclaimer, the term of this patent is extended or adjusted under 35 U.S.C. 154(b) by 6 days.

(21) Appl. No.: 10/169,576

(22) PCT Filed: May 8, 2002

(86) PCT No.: PCT/JP02/04464

§ 371 (c)(1),
(2), (4) Date: Jul. 25, 2002

(87) PCT Pub. No.: WO02/096322

PCT Pub. Date: Dec. 5, 2002

(65) Prior Publication Data

US 2003/0209452 A1 Nov. 13, 2003

(30) Foreign Application Priority Data

May 25, 2001 (JP) ........................................ 2001-157186

(51) Int. Cl.[7] .................................................. A61F 9/00
(52) U.S. Cl. ........................ 606/107; 206/5.1; 623/6.18
(58) Field of Search .................. 206/5.1, 438; 606/107; 623/6.11, 6.12, 6.18

(56) References Cited

U.S. PATENT DOCUMENTS

| | | | |
|---|---|---|---|
| 5,139,501 A | * | 8/1992 | Klass |
| 5,171,241 A | | 12/1992 | Buboltz et al. |
| 5,281,227 A | * | 1/1994 | Sussman |
| 5,616,148 A | | 4/1997 | Eagles et al. |
| 5,803,925 A | | 9/1998 | Yang et al. |
| 6,537,282 B1 | * | 3/2003 | Pynson et al. |

FOREIGN PATENT DOCUMENTS

| | | |
|---|---|---|
| JP | A 4-212350 | 8/1992 |
| JP | A 9-501574 | 2/1997 |

\* cited by examiner

Primary Examiner—David T. Fidei
(74) Attorney, Agent, or Firm—Oliff & Berridge, PLC

(57) ABSTRACT

A storage case having a soft intraocular lens folding function, which has a constitution with excellent reliability and manufacturability, is capable of sterilely storing an intraocular lens produced in a production line without damaging it until a time of surgery, and enables an operator to perform an operation of picking a soft intraocular lens L with an extractor with ease and reliability, is provided. In the storage case having a soft intraocular lens folding function, which includes a base part 10, a movable part 40 and a lid part 70, the aforementioned base part 10 is slidably joined to the aforementioned movable part 40, and the lid part 70 is attachably and detachably fitted therein, thus making it possible to store the lens L sterilely without damaging it, and during a surgery, the lens L can be folded with ease and reliability by pressing a lever portion 42 at the movable part 40.

9 Claims, 11 Drawing Sheets

SECTIONAL VIEW TAKEN ALONG C-C LINE

SECTIONAL VIEW TAKEN ALONG D-D LINE

STORAGE CASE HAVING SOFT INTRAOCULAR LENS FOLDING FUNCTION

TECHNICAL FIELD

The present invention relates to a storage case having a soft intraocular lens-folding function, which houses and stores a soft intraocular lens used in cataract operations and the like, and also has a function of folding the soft intraocular lens on the occasion of a surgical operation.

BACKGROUND ART

For example, in a cataract operation, the aim is to restore sight by a surgical procedure, which inserts into the eye an intraocular lens, which is an artificial lens, in place of a natural lens that has become opaque due to a cataract.

This intraocular lens has a circular optical lens portion, and arm-shaped supporting portions extended in an arc form to an outside from a lens edge portion to stabilize this lens portion inside the eye.

As this intraocular lens, there has been provided in recent years a soft intraocular lens of which optical lens portion can be deformed by being folded in two using silicon resin, acrylic resin, hydrogel and other such materials.

This soft intraocular lens can be inserted into the eye of a patient with the lens portion being in a folded state, and therefore it has numerous clinical advantages such as making the size of the incision smaller at the time of surgery and faster recovery after surgery.

When attaching this soft intraocular lens, the optical lens portion must be folded beforehand prior to inserting the soft intraocular lens into the eye.

As methods for carrying out this folding operation, in the past there was a method, which makes use of a special forceps-shaped tool called an extractor, and a method, which makes use of a special jig called an injector.

As an example of the method that uses an extractor, the method of using two extractors will be explained. Firstly, a first extractor is held in the right hand, then the end or the support portion of the lens portion is clamped, and the lens is taken out of the lens case. Next, the center portion of the lens portion is clamped with a second extractor held in the left hand, and the lens portion is folded using the first extractor held in the right hand. Before the lens portion is completely folded, the second extractor with which the center portion of the lens portion is clamped is removed. The lens portion is completely folded with the first extractor and the lens is inserted into the eye.

In the method that uses an injector, after setting an intraocular lens inside the injector, the tip of that injector is inserted into the insertion part of the eye, the extrusion aperture of the injector is operated, and the lens is inserted into the eye from the tip of the injector (publication of Japanese Patent application No. 4-212350, for example).

Furthermore, as the other methods, there has been proposed a method, which makes use of the intraocular lens folder disclosed in Published Japanese translation of PCT international publication for patent application No. 9-501574. This intraocular lens folder is constituted such that two pairs of opposing jaws are formed respectively in a pair of pliers-shaped lever handles, and the edge of a lens is placed in and held by four supporting portions formed by these 2 pairs of jaws, and in addition, by squeezing these lever handles, the gap of the pair of jaws of one side is made narrower, while at the same time, the gap of the pair of jaws of the other side is made wider.

If this tool is used, when the lens portion being held by the two pairs of jaws is folded by being put between the pair of jaws of the one side, it is possible to make the pair of jaws of the other side open and recede so as not to impede the folding thereof, and therefore, folding can be performed with a lens being held as-is.

However, the inventors have clearly shown that the above-described arts have the following problems.

That is, in the method in which two extractors are used as mentioned firstly, a problem is that operation is complicated, a problem is that it is difficult to accurately hold the center portion of a lens, and a problem is that there is the danger of dropping a lens when switching an extractor from one hand to the other and when re-holding the lens. Another problem is that since the center portion of a lens is clamped and held by an extractor, the center portion of the lens that is the most important from the standpoint of optics is apt to be damaged by the extractor.

The secondarily-mentioned method in which an injector is used appears at a glance to be simple and reliable, but actually, if an intraocular lens is not set inside an injector precisely from the standpoint of the injector mechanism, there is the danger of the intraocular lens getting stuck inside the injector, and either not being able to be injected, or not being injected into the proper position. With this method, the problem is that it was not always easy to set an intraocular lens precisely inside an injector.

In the thirdly-mentioned method in which a lens folder is used, a problem is that the structure is complex and it is apt to become very costly since two different linkage operations, i.e. narrowing the gap of one side of the two pairs of jaws, while at the same time widening the gap of the other side must be carried out. In addition, a problem is that, when folding a lens portion by manually operating the lever handle, if there is a mistake in the degree of force used in operating this handle, there is apt to be damage done to the lens portion by the application of unreasonable force to the lens portion. Furthermore, the folding of a lens portion must be carried out by holding the edge portion of the lens in the proper position over the four supporting portions formed by the two pairs of jaws, but a problem is that this operation is also unexpectedly troublesome, and considerable concentration is required to perform this properly. This is because, if the lens portion holding position is inaccurate, not only is it not possible to fold the lens portion accurately, there is also the danger that the lens will slip off during folding.

The above-described problems are serious problems under the situation of an ophthalmologic surgery.

This is because pressure is always put on the operators under the ophthalmologic surgery to carry out extremely accurate operations in minimal time. Consequently, it is necessary for the operators to carry out the operations other than the surgical operations for patients in minimal time and under low load.

Further, for the purpose of folding a lens, using a plurality of instruments and requiring a plurality of stages of operation have the possibility of giving an unfavorable influence in keeping a good sanitary condition of lens and in preventing lens from being damaged.

That is, the larger the number of instruments becomes and the more complicated the shape becomes, the more difficult the sterilization operation becomes, and each time a lens is moved from one instrument to another, the possibility of damaging the lens increases Consequently, an object of the present invention is to provide a storage case having a soft intraocular lens folding function, which has a constitution offering superb reliability and manufacturability, which can aseptically store an intraocular lens produced in a production line without damaging it until the time of a surgery, and which enables an operator to perform an operation of clamping the stored lens with an extractor easily and reliably.

DISCLOSURE OF THE INVENTION

A first invention to solve the above-described problems is a storage case having a soft intraocular lens folding function characterized in that the first invention comprises a base part, a movable part and a lid part, the aforesaid base part comprises a base part side joining portion which is slidably joined to the aforesaid movable part, a base part side holding portion which supports a soft intraocular lens, a base part side lens pressing portion which presses the soft intraocular lens, and a base part side fitting portion which is attachably and detachably fitted into the aforesaid lid part, the aforesaid movable part comprises a movable part side joining portion which is slidably joined to the aforesaid base part, a lever portion, a movable part side holding portion which supports the soft intraocular lens, and a movable part side lens pressing portion which presses the soft intraocular lens, the aforesaid lid part comprises a lid part side fitting portion which is attachably and detachably fitted into the aforesaid base part, the aforesaid lid part protects the soft intraocular lens held by the base part side holding portion and the movable part side holding portion and the aforesaid movable part by being fitted into the aforesaid base part, when the aforesaid lid part is detached from the aforesaid base part and the lever portion is pressed, the soft intraocular lens held by the base part side holding portion and the movable part side holding portion is pressed by the base part side lens pressing portion and the movable part side lens pressing portion, and is appropriately folded.

As a result of adopting the above-described constitution, by pressing the aforesaid lever portion and folding the lens, a load exerted when the lens is picked is reduced, and by integrating the functions of storing and folding the lens, an operation of moving the lens from the storage case to a folding device is made unnecessary, thus reducing the possibility of damaging the lens when the lens is moved.

A second invention is a storage case having a soft intraocular lens folding function characterized in that the second invention comprises a base part, a movable part and a lid part, the aforesaid base part comprises a base part side joining portion which is slidably joined to the aforesaid movable part, a base part side holding portion which supports a soft intraocular lens, a base part side lens pressing portion which presses the soft intraocular lens, and a base part side fitting portion which is attachably and detachably fitted into the aforesaid lid part, the aforesaid movable part comprises a movable part side joining portion which is slidably joined to the aforesaid base part, a lever portion, a spring portion which causes a proper elastic repulsive force between the lever portion and the aforesaid base part when the lever portion is pressed, a movable part side holding portion which supports the soft intraocular lens, and a movable part side lens pressing portion which presses the soft intraocular lens, the aforesaid lid part comprises a lid part side fitting portion which is attachably fitted into the aforesaid base part, the aforesaid lid part protects the soft intraocular lens held by the base part side holding portion and the movable part side holding portion and the aforesaid movable part by being fitted into the aforesaid base part, when the aforesaid lid part is detached from the aforesaid base part and the lever portion is pressed, the soft intraocular lens held by the base part side holding portion and the movable part side holding portion is pressed by the base part side lens pressing portion and the movable part side lens pressing portion, and is appropriately folded.

As a result of adopting the above-described constitution, when the lens starts to be folded by pressing the aforesaid lever portion, a suitable elastic repulsive force occurs due to the effect of the aforesaid spring portion between the aforesaid lever portion and the aforesaid base part, whereby the lens can be folded at a desired speed while the feeling of it is made certain, thus reducing a load exerted when the lens is picked, and by integrating the functions of storing and folding the lens, an operation of moving the lens from the storage case to the folding device is made unnecessary, thus eliminating the possibility of damaging the lens when the lens is moved.

A third invention is the storage case having the soft intraocular lens folding function according to the first or the second invention, characterized in that when the lever portion is pressed, a moving distance of the lever portion and a moving distance of the movable part side lens pressing portion are equal.

As a result of adopting the constitution in which the moving distance of the aforesaid lever portion and the moving distance of the aforesaid movable part side lens pressing portion are equal, the movement of the movable part side lens pressing portion and the movement of the pressing operation can be always grasped as equivalent intuitively and directly when the lever portion is pressed, and therefore the concentration of consciousness on this portion can be greatly reduced.

A fourth invention is the storage case having the soft intraocular lens folding function according to any one of the first to third invention, characterized in that the aforesaid base part and the aforesaid movable part have soft intraocular lens supporting pins, when the lever portion is not pressed, the soft intraocular lens supporting pins support the soft intraocular lens, when the lever portion is pressed, the base part side soft intraocular lens supporting pin is stored in the movable part side lens pressing portion and the movable part side soft intraocular lens supporting pin is stored in the base part side lens pressing portion.

As a result of adopting this constitution, both the lens supporting pins of the base part and the movable part are stored in the opposing lens pressing portions, and they do not hinder the movement of the extractor, and therefore the lens can be picked with ease and reliability.

A fifth invention is the storage case having the soft intraocular lens folding function according to any one of the first to fourth invention, characterized in that in the base part side lens pressing portion and the movable part side lens pressing portion, portions which hold the soft intraocular lens are overhung relative to planes formed by the base part side holing portion and the movable part side holding portion.

As a result of adopting this constitution, when the lever portion is pressed, the aforesaid soft intraocular lens is caught by the overhang surface of the base part side lens pressing portion and the overhand surface of the movable part side lens pressing portion, and is folded upward in a convex shape in a stable state.

A sixth invention is the storage case having the soft intraocular lens folding function according to any one of the first to fifth invention, characterized in that in the base part side lens pressing portion and the movable part side lens pressing portion, extractor guides are provided at surfaces with which an extractor is in contact when the folded soft intraocular lens is picked with the extractor.

As a result of adopting this constitution, an irregular movement of the tip end of the extractor, which is caused by a slight trembling of a hand and the like when the lens is picked, is eliminated, and therefore the folded soft intraocular lens can be picked with accuracy and ease.

A seventh invention is the storage case having the soft intraocular lens folding function according to any one of the first to the sixth invention, characterized in that the aforesaid base part and the aforesaid lid part are provided with light through-hole which is used for performing inspection and/or measurement of the soft intraocular lens by emitting light to the soft intraocular lens from an outside of the aforesaid storage case in a state in which the aforesaid lid part protects the soft intraocular lens and the aforesaid movable part by being fitted into the aforesaid base part.

As a result of adopting this constitution, it is made possible to confirm the optical characteristics of the lens stored in the storage case without detaching the lid part.

A eighth invention is the storage case having the soft intraocular lens folding function according to any one of the first to seventh invention, characterized in that the eight invention further comprises a control part which controls turning of the soft intraocular lens.

As a result of adopting this constitution, the turning of the aforesaid soft intraocular lens due to, for example, vibrations, impacts from outside and the like is controlled, and therefore the aforesaid soft intraocular lens is folded at a preferable position.

A ninth invention is the storage case having the soft intraocular lens folding function according to the eighth invention, characterized in that the aforesaid control part comprises columnar projections provided at the aforesaid base part and controls movement of arm-shaped supporting portions provided at the soft intraocular lens.

As a result of adopting this constitution, the turning of the aforesaid soft intraocular lens can be controlled without touching the optical surface of the aforesaid soft intraocular lens.

Figure 1:
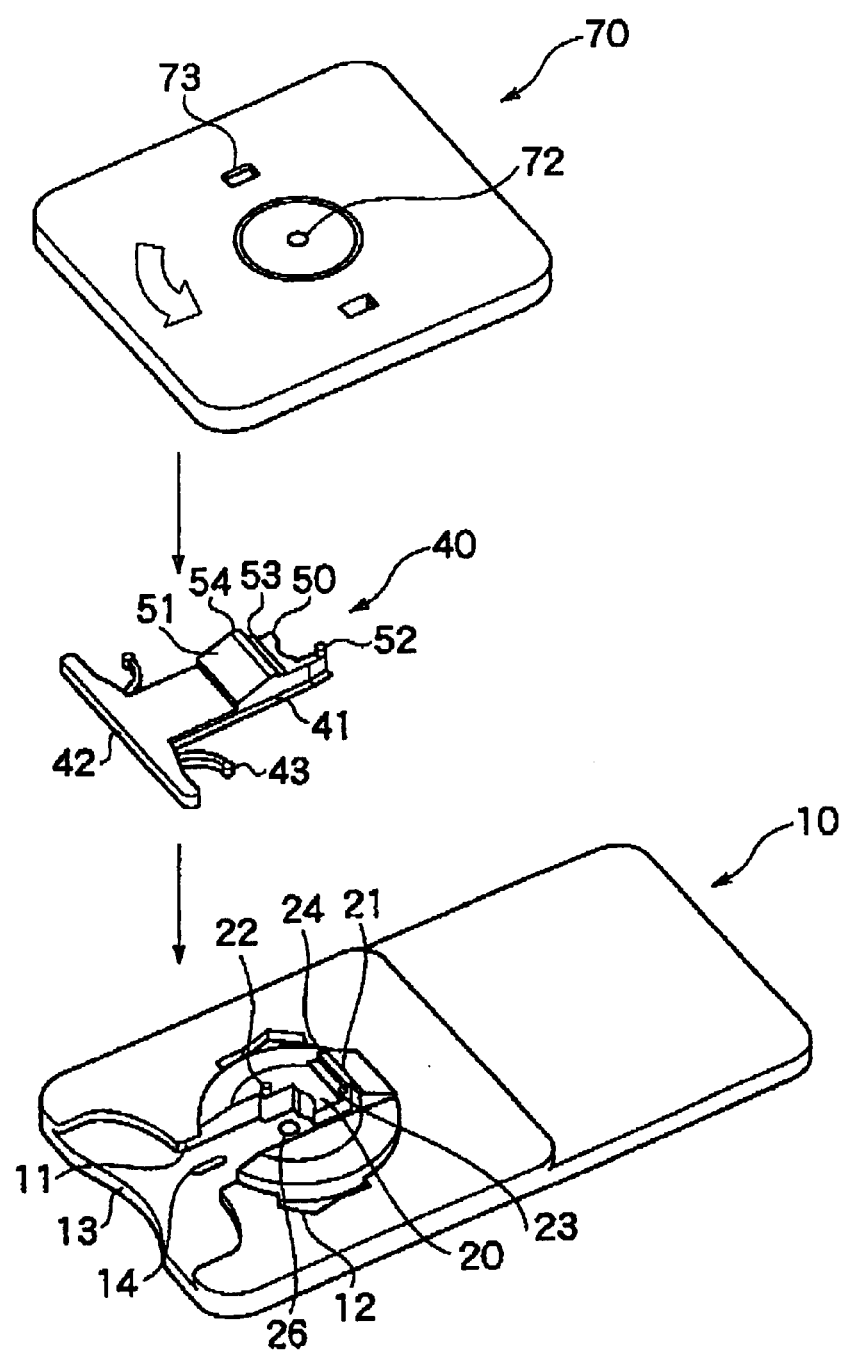
FIG. 1 is a perspective view of a top surface side of each part of a storage case according to the present invention.

10 . . . BASE PART, 11 . . . BASE PART SIDE JOINING PORTION, 12 . . . BASE PART SIDE FITTING PORTION, 20 . . . BASE PART SIDE HOLDING PORTION, 21 . . . BASE PART SIDE LENS PRESSING PORTION, 22 . . . BASE PART SIDE LENS SUPPORTING PIN, 23 . . . OVERHANG SURFACE OF BASE PART SIDE LENS PRESSING PORTION, 24 . . . BASE PART SIDE EXTRACTOR GUIDE, 26 . . . BASE PART LIGHT THROUGH-HOLE, 27 . . . RECTANGULAR PARALLELEPIPED PROJECTION (CONTROLLING PART), 28 . . . CYLINDRICAL PROJECTION (CONTROLLING PART), 40 . . . MOVABLE PART, 41 . . . MOVABLE PART SIDE JOINING PORTION, 42 . . . LEVER PORTION, 43 . . . SPRING PORTION, 50 . . . MOVABLE PART SIDE HOLDING PORTION, 51 . . . MOVABLE PART SIDE LENS PRESSING PORTION, 52 . . . MOVABLE PART SIDE LENS SUPPORTING PIN, 53 . . . SURFACE OF MOVABLE PART SIDE LENS PRESSING PORTION, 54 . . . MOVABLE PART SIDE EXTRACTOR GUIDE, 70 . . . LID PART, 71 . . . LID PART SIDE FITTING PORTION, 72 . . . LID PART LIGHT THROUGH-HOLE, L . . . SOFT INTRAOCULAR LENS, L1 . . . SUPPORTING PORTION OF SOFT INTRAOCULAR LENS EXTENDING IN DIRECTION OF MOVABLE PART SIDE LENS PRESSING PORTION, L2 . . . SUPPORTING PORTION OF SOFT INTRAOCULAR LENS EXTENDING IN DIRECTION OF BASE PART SIDE LENS PRESSING PORTION

BEST MODE FOR CARRYING OUT THE INVENTION

Aspects of the embodiment of the present invention will be explained in detail hereinbelow by referring to the drawings. The parts corresponding to each of the drawings are shown by being given the identical reference numerals and symbols.

Figure 2:
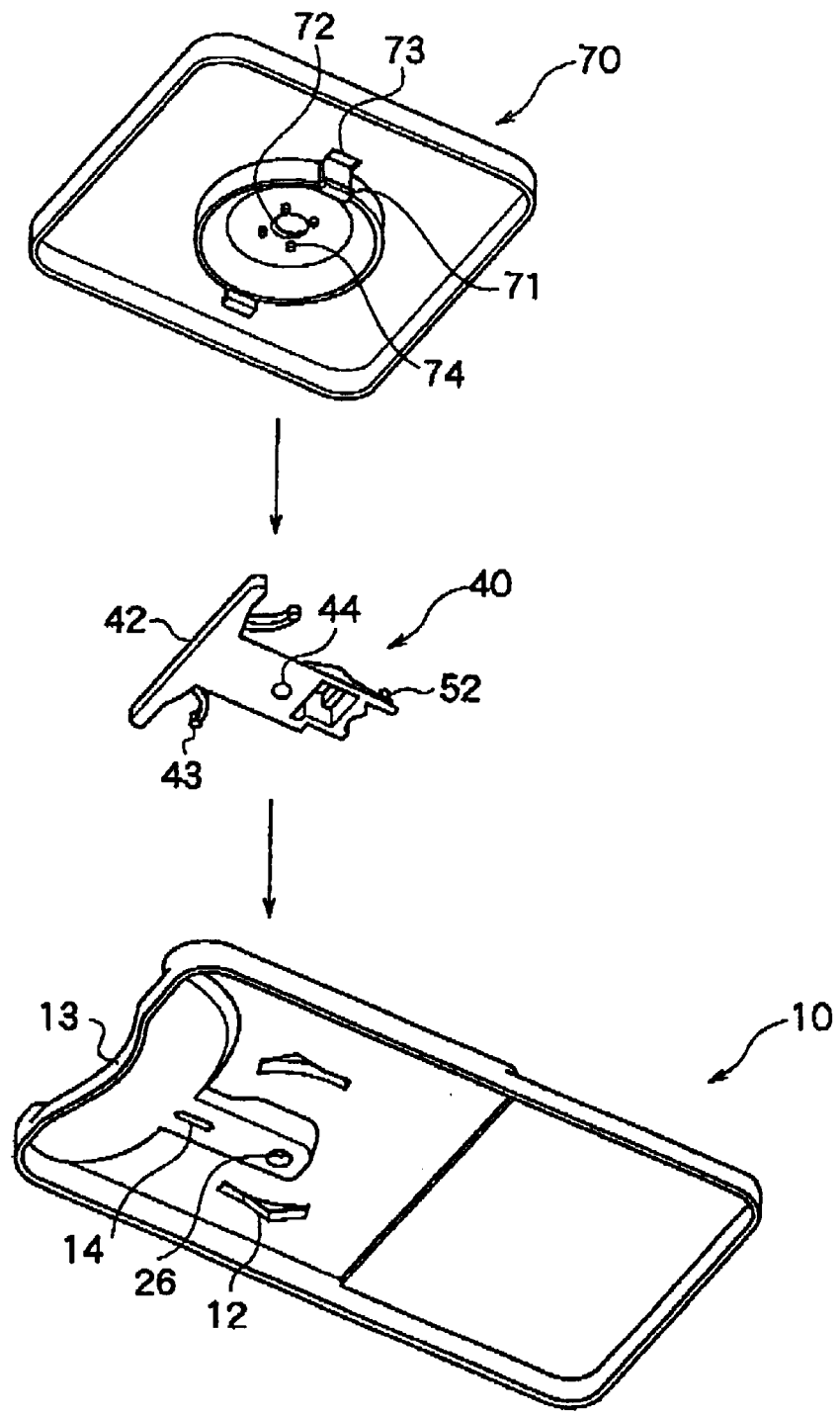
FIG. 2 is a perspective view of a bottom surface side of each part of the storage case according to the present invention.

FIG. 1 is an exploded perspective view of a base part 10, a movable part 40, and a lid part 70 constituting a storage case having a soft intraocular lens folding function (hereinafter, called a storage case), which are seen from above, according to the embodiment of the present invention, and FIG. 2 is an exploded perspective view of the aforementioned base part 10, movable part 40 and lid part seen from below.

Figure 3:
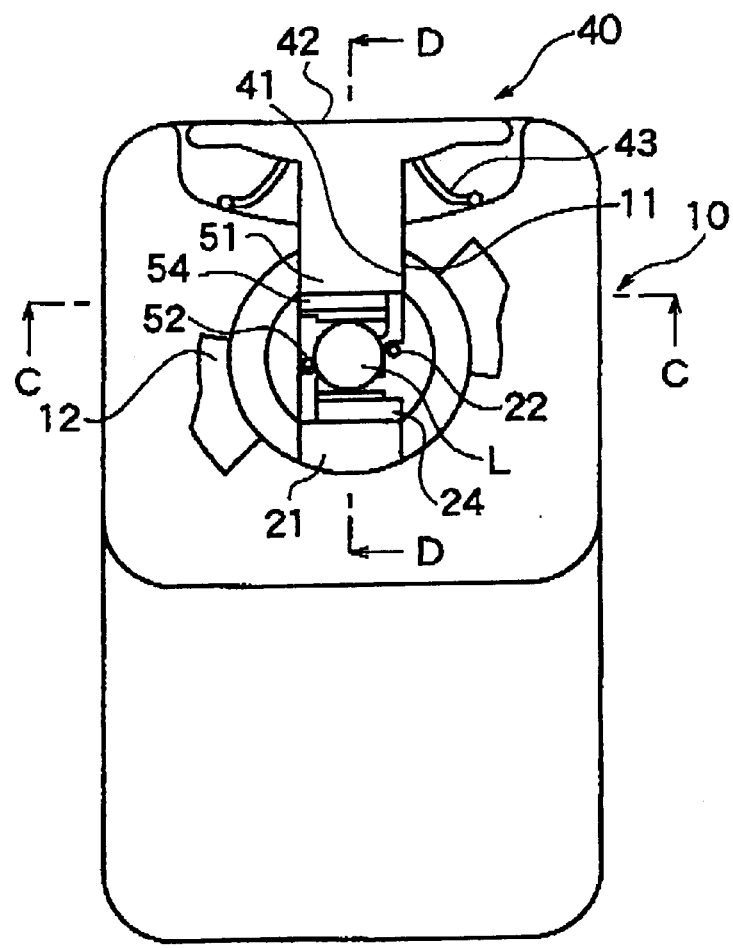
FIG. 3 is a plan view of the storage case according to the present invention.
Figure 4:
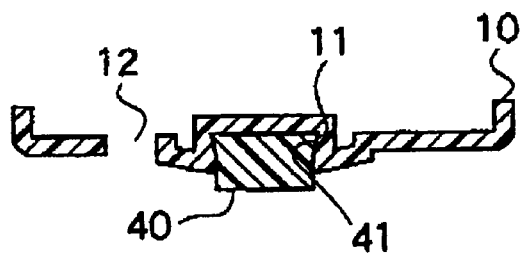
FIG. 4 is a sectional view taken along the line C—C in FIG. 3.
Figure 5:
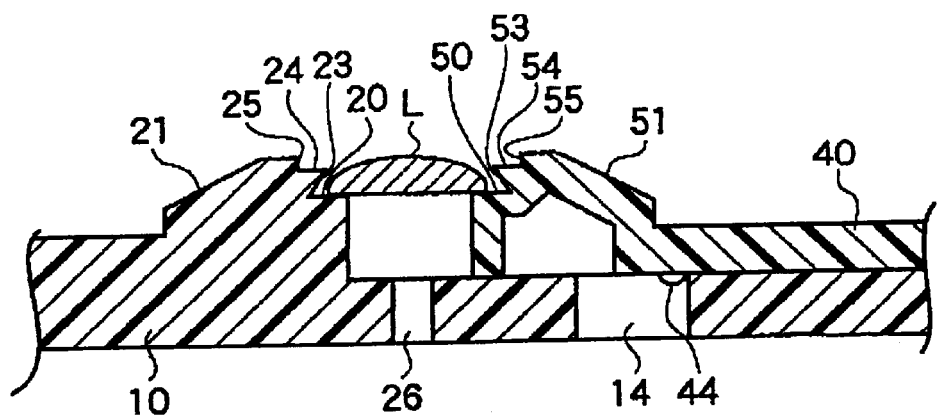
FIG. 5 is a sectional view taken along the line D—D in FIG. 3.

FIG. 2 is a top view of a state in which the aforementioned base part 10 and the movable part 40 are joined to each other, and the view showing a sectional position of a sectional view taken along the C—C line in FIG. 3 that is shown in FIG. 4, and a sectional view of the D—D line in FIG. 3 shown in FIG. 5.

Figure 6:
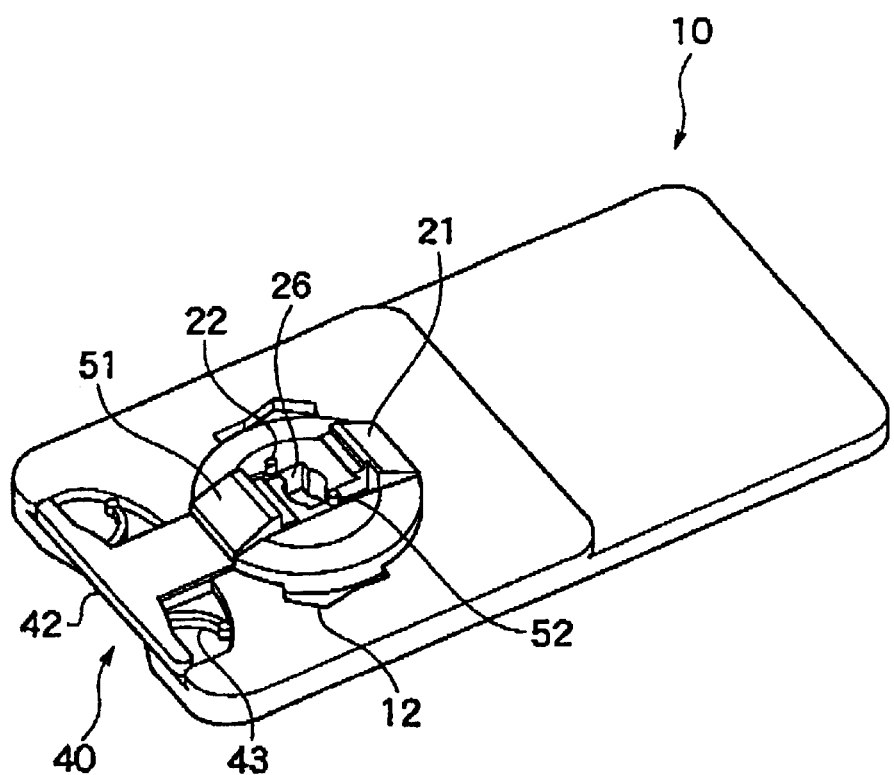
FIG. 6 is a perspective view of a situation in which a movable part is joined to a base part in the storage case according to the present invention.
Figure 7:
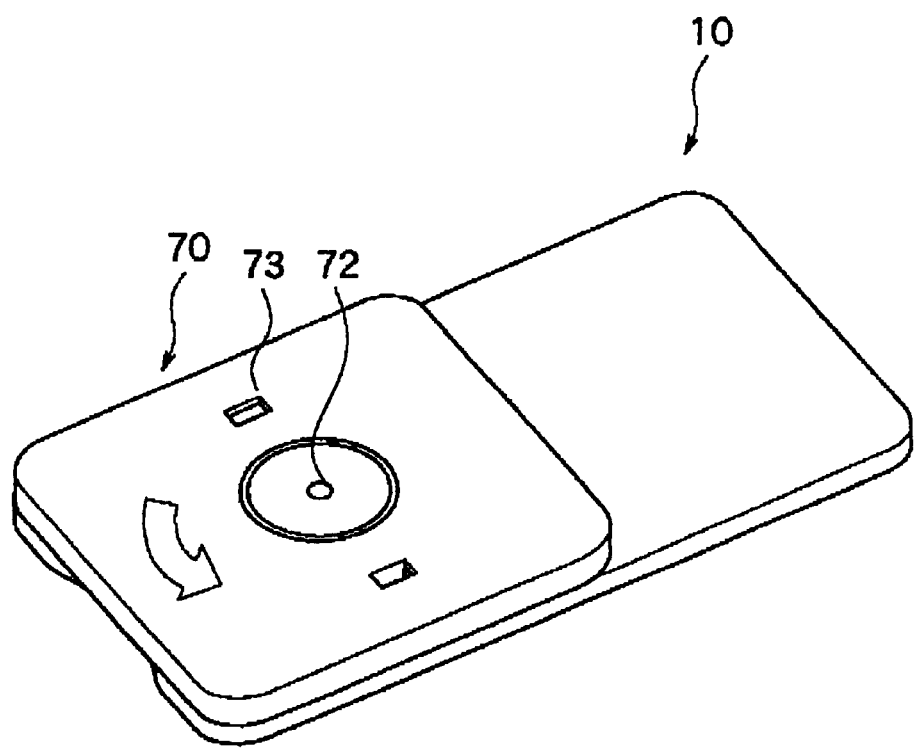
FIG. 7 is a perspective view of a situation in which the movable part is joined to the base part and a lid part is fitted therein in the storage case according to the present invention.

FIG. 6 is a perspective view of a state in which the aforementioned base part 10 and the movable part 40 are joined to each other, and FIG. 7 is a perspective view of a state in which a lid part 70 is further fitted into the base part 10 and the movable part 40 shown in FIG. 6.

Figure 8:
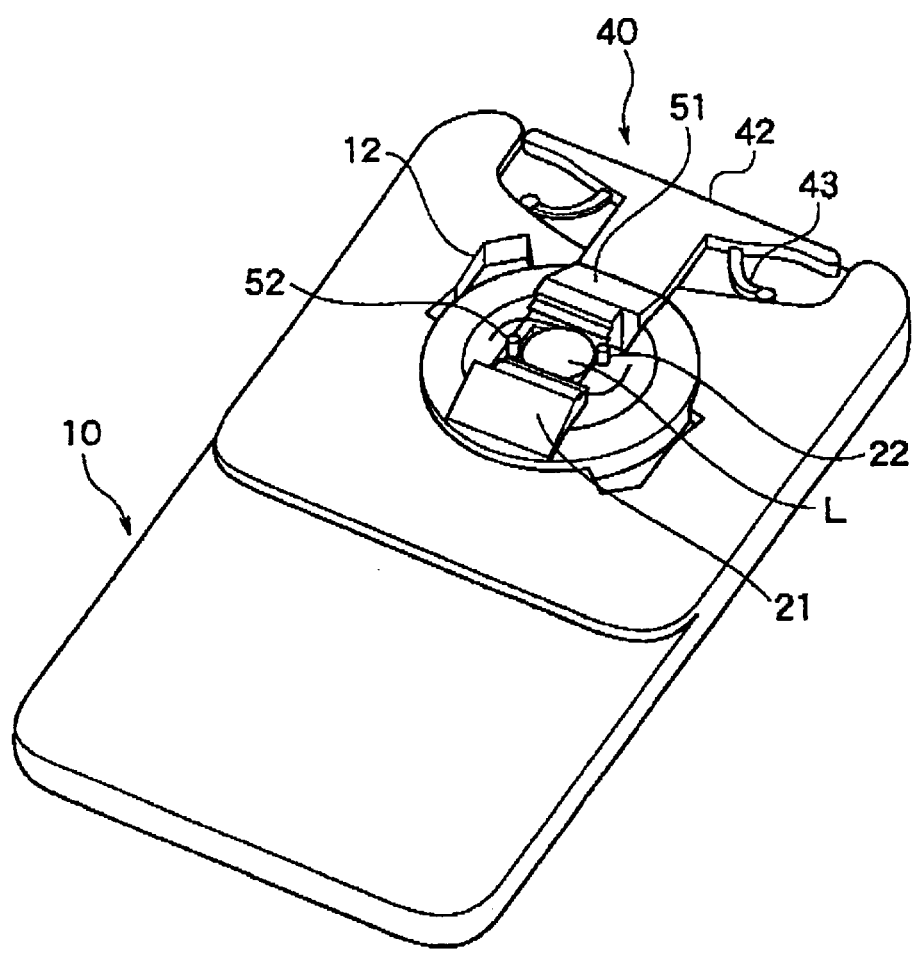
FIG. 8 is a perspective view of a situation in which a lens is stored in the storage case shown in FIG. 6.
Figure 9:
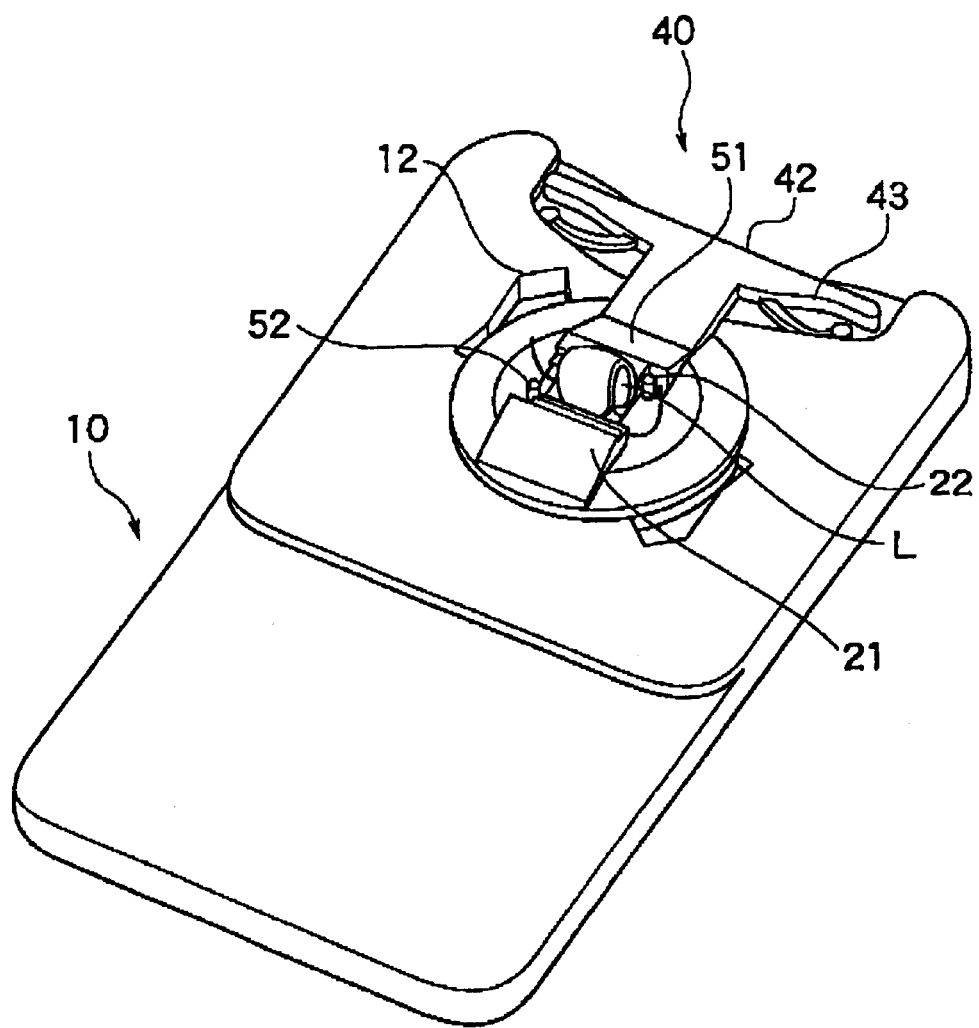
FIG. 9 is a perspective view of a situation in which the lens is folded by pressing a lever portion of the storage case shown in FIG. 8.

FIG. 8 is a perspective view of a state in which a soft intraocular lens (hereinafter, called a lens) L is stored in the storage case which is formed by joining the aforementioned base part 10 and the movable part 40, and FIG. 9 is a perspective view of a state in which the lens L is finished being folded by pressing a lever portion 42 described later in the storage case storing the lens L shown in FIG. 8.

Figure 10:
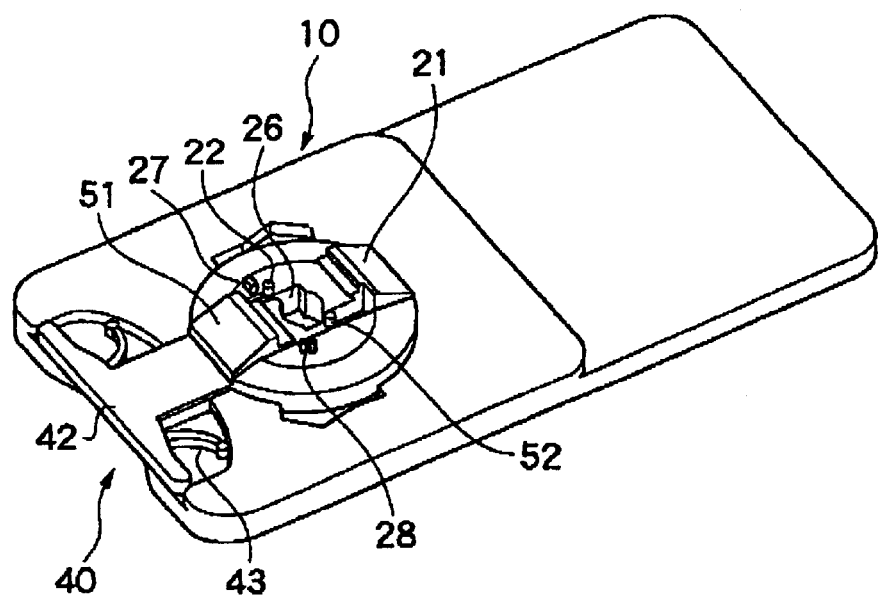
FIG. 10 is a perspective view of a situation in which the movable part is joined to the base part in the storage case according to another embodiment.
Figure 11:
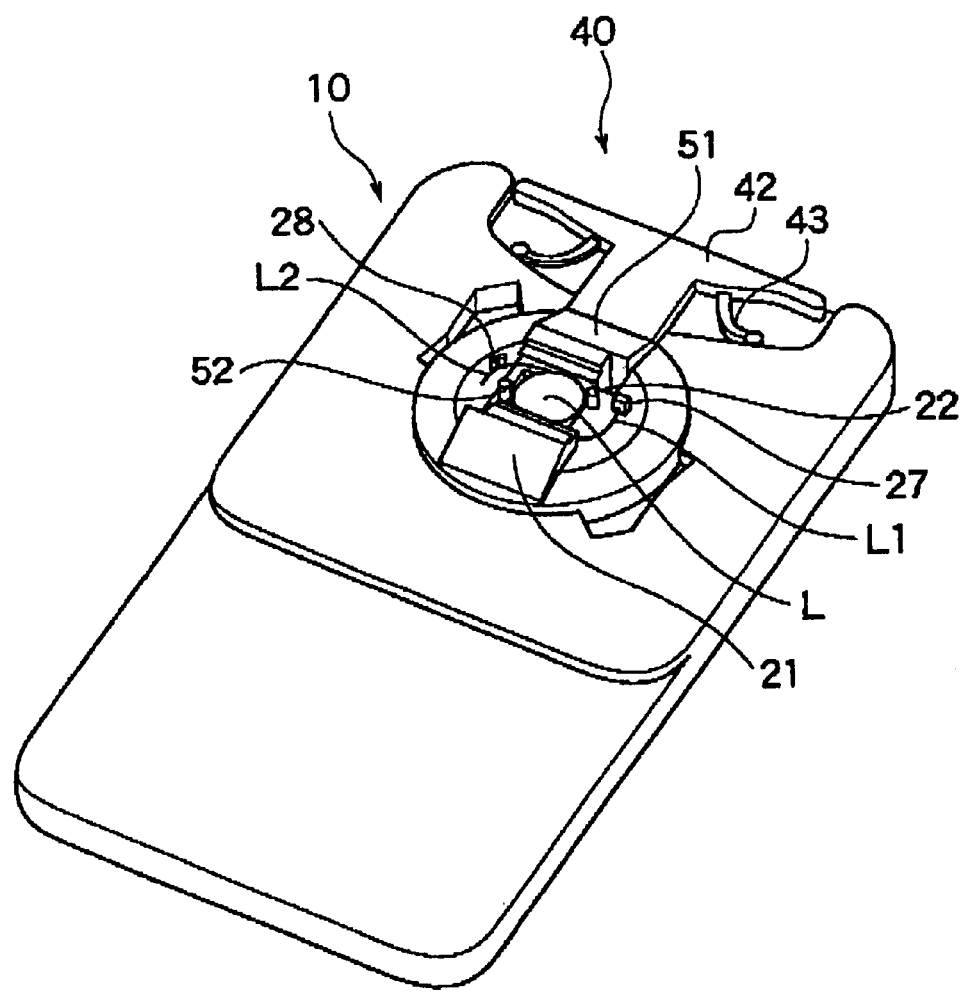
FIG. 11 is a perspective view of a situation in which the lens is stored in the storage case shown in FIG. 10.
Figure 12:
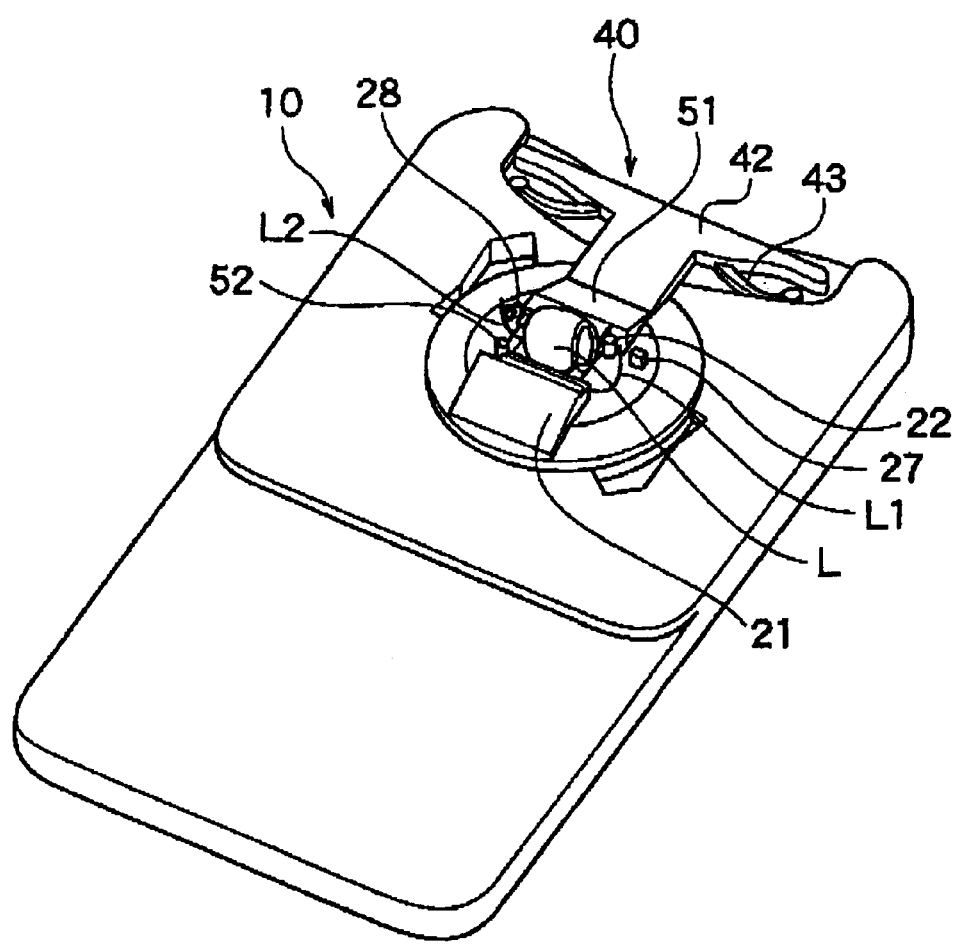
FIG. 12 is a perspective view of a situation in which the lens is folded by pressing the lever portion of the storage case shown in FIG. 10.

FIG. 10 is a perspective view of a state in which the aforementioned base part 10 and the movable part 40 according to another embodiment are joined to each other, FIG. 11 is a perspective view of a state in which the lens L is stored in the storage case formed by joining the aforementioned base part 10 and the movable part 40 shown in FIG. 10, and FIG. 12 is a perspective view of a state in which the lens L is finished being folded by pressing the lever portion 42 described later in the storage case storing the lens L shown in FIG. 11.

A constitution of each part of the storage case according to an example of the embodiment will be firstly explained with reference to FIG. 1 to FIG. 5.

The storage case seen from above, which is shown in FIG. 1, has the base part 10, the movable part 40 and the lid part 70. Each portion will be separately explained hereinafter.

First, the base part 10 is provided with a base part side joining portion 11 which is joined to the movable part 40, a base part side fitting portion 12 for attachably and detachably fitting the base part 10 and the lid part 70, a base recessed part 13 for pressing the lever portion 42 that will be described later, a stopper joining hole 14 for controlling the movement of the movable part 40 that will be described later, and a base part side holding portion 20 for holding the lens L. The base part side holding portion 20 is further provided with a base part side lens pressing portion 21, a base part side lens supporting pin 22, an overhang surface 23 of the base part side lens pressing portion for catching the lens L that will be described later when pressing the lens L, a base part side extractor guide 24 for guiding an extractor of an operator, that picks the lens L, and a base part light through-hole 26.

Next, the movable part 40 is provided with a movable part side joining portion 41 which is joined to the base part 10, a lever portion 42 which is pressed by fingers of an operator when folding the lens L, a spring portion 43 which generates a proper elastic repulsive force in contact with the base recessed portion 13, and a movable part side holding portion 50 which holds the lens L. The movable portion side holding portion 50 is provided with a movable part side lens pressing portion 51, a movable part side lens supporting pin 52, an overhang surface 53 of the movable part side lens pressing portion, which catches the lens L when pressing the lens L, that will be described later, and a movable part side extractor guide 54 which guides the extractor of an operator, that is to pick the lens L.

Furthermore, the lid part 70 is provided with a lid part light through-hole 72, and a lid part air hole 73 through which a gas is circulated during gas sterilization.

Referring to FIG. 2, each part of the storage case seen from below will be explained. The explanation of the portions explained in the above-described FIG. 1 will be omitted.

The movable part 40 is provided with a movable part stopper 44, which is a semicircular raised portion and controls the movement of the movable part 40 in conjunction with the aforementioned stopper joining hole 14.

The lid part 70 is provided with a lid part side fitting portion 71, which is attachably and detachably fitted into the base part side fitting portion 12 provided at the base, and a lid part lens supporting pin 74 which supports the lens L, which will be described later.

The base part 10, the movable part 40 and the lid part 70 are constituted with use of a material that can provide appropriate degrees of elasticity and rigidity, such as, for example, a fluororesin and polyamide resin. As this kind of material, resins, such as polyallylate, polyethylene threphthalate, polyvinylchroride, polycarbonate, polysulfon, polystyrene, polybutylene terephthalate, polypropylene, and polymethylpentene, metals, such as duralumin, stainless steel, and titanium, or a compound material that is made by combining the above-described resins, metals, and ceramics.

Especially when a resin or a compound material which can be injection-molded is used, only three parts that are the base part 10, the movable part 40 and the lid part 70 need to be molded, which makes the volume production possible at low cost.

FIG. 3 is a plan view of the occasion in which the movable part 40 is mounted on the base part 10, which is a view for showing cutting plane positions of sectional views shown as FIG. 4 (sectional view taken along the C—C line) and FIG. 5 (sectional view taken along the D—D line) next, and therefore the explanation will be omitted.

Next, by using FIG. 4, joining of the base part 10 and the movable part 40, and an operation thereof will be explained. In FIG. 4, the base part 10 is illustrated at an upper side of FIG. 4 and the movable part 40 is illustrated at a lower side of FIG. 4.

As shown in FIG. 4, a bottom surface side of the movable part side joining portion 41, which is provided at the movable part 40 to be joined to the base part 10, has a taper enlarged at a bottom surface side, while the base part side joining portion 11, which is provided at the base part 10 and is a joining portion to the movable part 40, has a taper narrowed at a top surface side, and thus the movable part 40 is joined to the base part 10 and is only longitudinally movable.

Furthermore, as explained with reference to FIG. 1 and FIG. 2, the movable part stopper 44 being a semicircular raised portion is provided on a back surface of the movable part 40, and this movable part stopper 44 and the stopper joining hole 14 on the base part 10 are joined to each other. After the base part 10 and the movable part 40 are joined to each other once, the movement range of the movable part 40 relative to the base part 10 is controlled. For example, such a movement as the lever portion 42 projects from an outer edge of the base part 10 is controlled, and the movable part 40 is held at a position in which the position of the lever portion 42 matches to the outer edge of the base part 10 occurring due to an elastic repulsive force occurring when the spring portion 43 contacts the base recessed portion 13 in this state.

Next, with use of FIG. 5, joining of the base part 10 and the movable part 40, and the lens L placed thereon will be explained.

The movable part 40 joined to the base part 10 is controlled in the moving range relative to the base part 10 by the combination of the movable part stopper 44 and the stopper joining hole 14, and thus preventing the situation in which the lens L is folded more than necessary, or the situation in which the lens L falls from the base part side holding portion 20 and the movable part side holding portion 50.

The base part light through-hole 26 is provided directly below the lens L of the base part 10, it becomes a passage of test light when optical characteristics of the lens L is reconfirmed, and becomes a passage for a sterilizing gas during gas sterilization of the lens L.

Furthermore, as explained in FIG. 1, the base part side holding portion 20 is provided with the base part side lens pressing portion 21, the base part side extractor guide 24 and the overhang surface 23 of the base part side lens pressing portion from the left side of FIG. 5, and a very small base part side step 25 is provided between the base part side lens pressing portion 21 and the base part side extractor guide 24.

Similarly, the movable part side holding portion 50 is provided with the movable part side lens pressing portion 51, the movable part side extractor guide 54 and the overhang surface 53 of the movable part side lens pressing portion from the right side of FIG. 5 as explained in FIG. 1, and a very small movable part side step 55 is provided between the movable part side lens pressing portion 51 and the movable part side extractor guide 54.

Next, with reference to FIG. 6 and FIG. 7, an external appearance of the storage case according to an example of the embodiment will be explained.

In the state in which the movable part 40 is joined to the base part 10 shown in FIG. 6, a top surface of the lever portion 42 provided at the movable part 40 and a top surface of the adjacent base part 10 become substantially the same plane, and a side surface of the same lever portion 42 and the side surface of the base part 10 adjacent thereto become substantially the same plane. The spring portion 43 abuts to the base part 10 with an appropriate degree of stress, and the movable part side lens pressing portion 51 and the movable part side lens supporting pin 52 oppose the base part side lens pressing portion 21 and the base part side lens supporting pin 22, respectively.

The base part light through-hole 26 exists in a center of an area at which the base part side lens pressing portion 21 and the movable part side lens pressing portion 51 oppose each other, and a hole-shaped base part side fitting portions 12 to attachably and detachably fit onto the lid part side fitting portions provided at the lid part 70 are provided at the left and right. The base part side fitting portion 12 is provided to penetrate the base part 10, and becomes a passage for a gas during the gas sterilization that will be described later.

As shown in FIG. 7, when the lid part 70 is further fitted onto the joining body of the base part 10 and the movable part 40, the above-described movable part side lens pressing portion, the movable part side lens supporting pin, the base part side lens pressing portion, the base part side lens supporting pin, the lever portion and the spring portion as well as the lens L are covered with the lid part 70 and protected and at the same time, unexpected movement of them are controlled.

Since the lid part 70 is provided with the lid part light through-hole 72 and the lid part air hole 73, it is possible to reconfirm the optical characteristics of the lens L with the lid part 70 being attached, and they serve as the passages for a gas during the gas sterilization that will be described later.

Next, with reference to FIG. 8 and FIG. 9, the relative movements of the movable part 40 and the base part 10 and folding of the lens L at the time of an operator pressing the lever portion 42 with his or her fingers will be explained.

In the state in which the lever portion 42 is not pressed as shown in FIG. 8, the lens L is held by the holding portion formed by the base part side holding portion 20 and the movable part side holding portion 50 explained in FIG. 5, and the longitudinal and lateral movement of the lens L is further controlled by the base part side lens pressing portion 21, the base part side lens supporting pin 22, the movable part side lens pressing portion 51, and the movable part side lens supporting pin 52.

As a result, even if the storage case vibrates or inclines, the lens L is held with stability.

In this embodiment, the supporting pins are provided at the base part and the movable part respectively as described above, but two supporting pins may be provided at the base part or the movable part as necessary.

As shown in FIG. 9, when the lever portion 42 is pressed, the portions other than the spring portion 43 in the movable part 40 are not deformed and move forward, and the space between the base part side holding portion 20 and the movable part side holding portion 50 is narrowed and they finally collide against each other. At this time, the lens L is caught by the overhang surface 23 of the base part side lens pressing portion explained in FIG. 5 and the overhang surface 53 of the movable part side lens pressing portion, and since the overhang surface 23 of the base part side lens pressing portion and the overhang surface 53 of the movable part side lens pressing portion are provided to overhang relative to a surface formed by the base part side holding portion 20 and the movable part side holding portion 50, the lens L is folded upward in a concave shape in a stable state.

If the advancing speed of the lever portion 42 is too high, there is the possibility that the lens L is sprung by elasticity of the lens L, goes out of the holding portion and falls off. This is the situation which should be avoided by all means since the fallen lens L cannot be attached to a patient.

However, it is not preferable to make the operator careful not to make the advancing speed of the lever portion 42 too high, because it further exerts burden on the operator under the pressure of the ophthalmological surgery.

Here, in the embodiment of the present invention, a balance can be taken between the elastic repulsive force occurring as the result of the aforementioned spring portion 43 abutting against the base portion 10 and a pressing force of the operator, thus obtaining the constitution for controlling the advancing speed without placing a burden on the operator. According to this constitution, the aforementioned advancing speed control is conducted by the balance between the elastic repulsive force and the pressing force of the operator, thereby making it possible to decrease the joining precision of the base part side joining portion 11 and the movable part side joining portion 41, which is the joining portion of the aforementioned movable part and the base part.

As a result, when the base part 10, the movable part 40, and the lid part are produced by being molded of resin, for example, it is possible to adopt injection molding and the like which makes volume production possible at low cost, thus making it possible to contribute to production cost reduction of the storage case.

To be additionally preferable, as the result of adopting this constitution, if an operation does not proceed with the folding of the lens L in a desired shape, the movable part 40 retreats by only loosening the pressing force temporarily, and therefore it is possible to fold the lens again.

In addition to the above, when the lever portion 42 is pressed, the movable part 40 other than the spring portion 43 advances without being deformed, and therefore the moving distances of the lever portion 42 and the movable part side lens pressing portion 51 for pressing the soft intraocular lens become equal. As a result, an operator can intuitively and directly grasp the movement of the movable part side lens pressing portion 51 as the movement of his or her own fingers, and therefore concentration of consciousness onto this portion can be reduced dramatically.

Further, simplification of the constitution of this portion eliminates the possibility of malfunction.

In addition to the above, as the constitution of the spring portion 43 in this embodiment, a plate spring constitution having the integral constitution with the lever portion 42 is adopted.

By adopting this constitution, projections and depressions or the shaded portions do not exist in the constitution of the spring portion 43, and therefore a gas sterilization operation can be easily and completely performed. Further, since the constitution is simple, malfunction and a trouble do not occur, production by injection-molding and the like is easy and design and production of a metal mold used for injection-molding of it are easy, thus making it possible to reduce total cost of production.

Further, when the movable part 40 is produced by injection-molding of a resin material or the like, because of elasticity which the desired resin material or the like has, it is easy to control the elastic repulsive force of the spring portion by controlling a set angle of the spring portion 43 relative to the movable part 40, thickness of the spring portion 43 and the like.

Meanwhile, the spring portion 43 can take an integral constitution with the base part 10 as desired, and it can take a helical spring constitution.

As another embodiment of the present invention, it may have the constitution in which an appropriate frictional force is caused to occur between the base part side joining portion 11 provided at the base part 10 and the movable part side joining portion 41 provided at the movable part 40 instead of providing the aforementioned spring portion 43, and the advancing speed of the movable part 40 is controlled without giving a burden on the operator. In this situation, it is preferable to increase joining precision of the base part side joining portion 11 and the movable part side joining portion 41.

According to the constitution, since the spring portion 43 is not required, when the material of the movable part 40 is selected, it is not necessary to consider elastic force possessed by the material, thus making it possible to expand the range of the material selection.

According to this constitution, the advancing speed of the movable part 40 can be controlled without giving a burden to an operator, and the movable part 40 advances without being deformed, thus equalizing the moving distances of the lever portion 42 and the movable part side lens pressing portion 51 for pressing the soft intraocular lens. As a result, the operator can always grasp the movement of the movable part side lens pressing portion 51 as his or her own fingers intuitively and directly, and thus concentration of consciousness onto this portion can be reduced dramatically. Furthermore, a gas sterilization operation can be performed easily and completely.

When the lever portion 42 is sufficiently pressed, the base part side holding portion 20 and the movable part side holding portion 50 explained in FIG. 5 collide against each other. At this time, the constitution is such that the lens L is folded upward in a convex shape as shown in the drawing, and is stored in the lens pressing portions opposing each other together with the both lens supporting pins 22 and 52, and therefore the movement of the extractor is not hindered, thus enabling the operator to hold an extractor in his or her dexterous hand and pick the lens L surely and easily.

That is, after holding the storage case in his or her non-dexterous hand, for example, and removing the lid part 70, the operator can easily and surely pick the lens L with an extractor without requiring passing the storage case from one hand to another and the like other than moving the fingers.

Since the storage case, the outer shape of the lever portion 42, and the state of the folded lens L are laterally symmetrical, the operator can hold the storage case and pick the lens L irrespective of whether the operator's dexterous hand is right or left.

Further, the movable part side lens pressing portion 51 which the aforementioned extractor touches is provided with the movable part side extractor guide 54 explained in FIG. 5, and the base part side lens pressing portion 21 is provided with the base part side extractor guide 24, respectively. Consequently, when the lens L is picked with the extractor, the tip end of the extractor is controlled properly by sliding on both the extractor guides 24 and 54, and reaches the lens surface to start the motion to pick the lens L, and therefore irregular movement of the tip end of the extractor caused by small trembling and the like of the operator is removed.

Furthermore, the operator can recognize the very small base part side step 25 and the movable part side step 55 explained in FIG. 5, which are formed by the movable part side lens pressing portion 51 and the movable part side extractor guide 54, and the base part side lens pressing portion 21 and the base part side extractor guide 24, as a sense of touch transmitted through the extractor. As a result, the operator can confirm the position of the tip end of the extractor not only by using sight but also using the sense of touch, and therefore it becomes possible to reduce a load on the sight of an operator dramatically.

Owing to the effects described above, it becomes possible to reduce a load on the operator ideally.

Next, the advantages of the present invention in view of transportation and storage of the lens L will be explained again with use of FIG. 7.

The lens L produced in a production line is in the state as shown in FIG. 7 when the lens is stored in the storage case and thereafter, the lid part 70 is closed. In this situation, the lens L has its outer perimeter portion held three-dimensionally in a line contact and a point contact by the base part side and movable part side holding portions 20 and 50, the base part side and the movable part side lens supporting pins 22 and 52, and the lid part lens supporting pin 74 provided at the back surface of the lid part.

As a result, even if the storage case is turned over, or an impact is applied to the storage case, the lens L is held without damaging the optical surface of the stored lens L.

Measurement of the optical characteristics is performed for the lens L held in the storage case, and it goes through the gas sterilization process. The sterilization gas passes through the base part side fitting portion 12, the base part light through-hole 26, the lid part air hole 73 and the lid part light through-hole 72, and sterilizes the lens L, the base part 10 and the like. In this situation, the lens L is three-dimensionally held in a line contact and point contact as described above, and therefore the lens L is thoroughly sterilized by gas sterilization.

The storage case for which sterilization is completed is sterilely wrapped as it is and transported to an operating room. Here, at the time of a surgery, the sterile wrapping is broken and the lid part 70 is removed, and the lens L folded as described above can be picked up with an extractor. If necessary, the optical characteristics of the lens L stored in the storage case can be reconfirmed at a bedside without removing the lid part 70. This confirmation is the final confirmation at the bedside, and therefore the lens L, which is to be attached to a patient, can be confirmed with perfection.

Considering the above process, it is only the extractor that contacts the lens L before the lens L after sterilization is inserted into the eye of the patient, and thus an ideal state in view of sterilization is provided.

Here, depending upon the size and the friction coefficient of the lens L, it is considered that the lens L supported by the holding portion turns above the holding portion as a result of the storage case turning over, an impact and vibration applied to the storage case when the storage case is transported and stored. If the lens L is folded in the state in which the lens L is turned from a desired position and is picked with an extractor, the lens L is picked up in an unsuitable direction to insert it into the eye of a patient, since the lens L is provided with two arm-shaped support portions extending in an arc form outward from the edge portion.

Consequently, in order to prevent the above situation, it is preferable to provide a control part for controlling the lens L turning above the holding portions.

The control parts in various forms are applicable if only they meet the requirements that they can control turning of the lens L, they do not damage the lens L, and they do not become hindrance when the lens L is picked with an extractor, and an example thereof will be shown in FIG. 10 to FIG. 12.

The storage case provided with the control part shown in FIG. 10 is the same as the storage case with the movable part 40 joined to the base part 10 as shown in FIG. 6, and is the example in which a rectangular parallelepiped projection 27 and a cylindrical projection 28 are further provided as columnar projections on the base part 10 to the left and right of the movable part side lens pressing portion 51.

In FIG. 10, two cylindrical projections 28 stand side by side, but they may be rectangular parallelepiped projections, and similarly, the rectangular parallelepiped projection 27 may be a cylindrical projection.

FIG. 11 shows a state in which the lens L is held by the holding portion formed by the base part side holding portion 20 and the movable part side holding portion 50 explained in FIG. 5 in the state in which the lever portion 42 is not pressed.

Here, as explained in FIG. 8, the lens L is controlled in its longitudinal and lateral movement by the base part side lens pressing portion 21, the base part side lens supporting pin 22, the movable part side lens pressing portion 51 and the movable part side lens supporting pin 52.

The lens L is provided with the two arm-shaped supporting portions extended outward in an arc form from an edge portion of the lens, and in FIG. 11, the supporting portion extending in a direction of the movable part side lens pressing portion 51 is represented by L1, and the supporting portion extending in a direction of the base part side lens pressing portion is represented by 12.

In this situation, an end portion of the supporting portion L1 extending in the direction of the movable part side lens pressing portion 51 is made to abut against the rectangular parallelepiped projection 27, and a curve portion of the supporting portion L2 extending in the direction of the base part side lens pressing portion is made to abut against the cylindrical projection 28.

As a result, the lens L already controlled in its longitudinal and lateral movement is also controlled in its turning movement and held by the holding portion. In this state, when the lid part 70 explained in FIG. 7 is fitted therein, a load is hardly exerted on the optical portion of the lens L even if an impact and vibrations are added to the storage case during transportation and storage, and longitudinal, lateral and turning movement in the lens L can be controlled.

FIG. 12 shows a state in which the lever portion 42 is pressed in the storage case in FIG. 11.

When the lever portion 42 is pressed, the movable part 40 is moved forward, and since the rectangular parallelepiped projection 27 and the cylindrical projection 28 are provided at the base part 10, they are relatively behind the movable part side lens pressing portion 51. As a result, it is preferable because the projections do not become hindrance when the operator picks the lens L.

Industrial Availability

As explained in detail thus far, the present invention has the base part, the movable part and the lid part; the aforementioned base part has the base part side joining portion which is slidably joined to the aforementioned movable part, the base part side holding portion which supports a soft intraocular lens, the base part side lens pressing portion which presses tile aforementioned soft intraocular lens, and the base part side fitting portion which is attachably and detachably fitted into the aforementioned lid part; the aforementioned movable part has the movable part side joining portion which is slidably joined to the aforementioned base part, the lever portion, the movable part side holding portion which supports the aforementioned soft intraocular lens and the movable part side lens pressing portion which presses the aforementioned soft intraocular lens; the aforementioned lid part has the lid part side fitting portion which is attachably and detachably fitted into the aforementioned base part; the aforementioned lid part protects the aforementioned soft intraocular lens held by the aforementioned base part side holding portion and the aforementioned movable part side holding portion, and the aforementioned movable part by being fitted into the aforementioned base part; and when the aforementioned lid part is removed from the aforementioned base part and the aforementioned lever portion is pressed, the aforementioned soft intraocular lens held by the aforementioned base part side holding portion and the aforementioned movable part side holding portion is pressed by the aforementioned base part side lens pressing portion and the aforementioned movable part side lens pressing portion, and properly folded, whereby a load exerted when the lens is picked can be greatly reduced, and the operation of moving the lens from the storage case to a folding device is made unnecessary by integrating the functions of storing and folding the lens, thus realizing the elimination of the possibility of the lens being damaged at the time of moving the lens.

What is claimed is:

1. A storage case having a soft intraocular lens folding function, comprising:

a base part;

a movable part; and a lid part, wherein said base part comprises a base part side joining portion which is slidably joined to said movable part, a base part side holding portion which supports a soft intraocular lens, a base part side lens pressing portion which presses the soft intraocular lens, and a base part side fitting portion which is attachably and detachably fitted into said lid part, said movable part comprises a movable part side joining portion which is slidably joined to said base part, a lever portion, a movable part side holding portion which supports the soft intraocular lens, and a movable part side lens pressing portion which presses the soft intraocular lens, said lid part comprises a lid part side fitting portion which is attachably and detachably fitted into said base part, said lid part protects the soft intraocular lens held by the base part side holding portion and the movable part side holding portion and said movable part by being fitted into said base part, when said lid part is detached from said base part and the lever portion is pressed, the soft intraocular lens held by the base part side holding portion and the movable part side holding portion is pressed by the base part side lens pressing portion and the movable part side lens pressing portion, and is appropriately folded.

2. A storage case having a soft intraocular lens folding function, comprising:

a base part;

a movable part; and a lid part, wherein said base part comprises a base part side joining portion which is slidably joined to said movable part, a base part side holding portion which supports a soft intraocular lens, a base part side lens pressing portion which presses the soft intraocular lens, and a base part side fitting portion which is attachably and detachably fitted into said lid part, said movable part comprises a movable part side joining portion which is slidably joined to said base part, a lever portion, a spring portion which causes a proper elastic repulsive force between the lever portion and said base part when the lever portion is pressed a movable part side holding portion which supports the soft intraocular lens, and a movable part side lens pressing portion which presses the soft intraocular lens, said lid part comprises a lid part side fitting portion which is attachably and detachably fitted into said base part, said lid part protects the soft intraocular lens held by the base part side holding portion and the movable part side holding portion and said movable part by being fitted into said base part, when said lid part is detached from said base part and the lever portion is pressed, the soft intraocular lens held by the base part side holding portion and the movable part side holding portion is pressed by the base part side lens pressing portion and the movable part side lens pressing portion, and is appropriately folded.

3. The storage case having the soft intraocular lens folding function according to claim 1, wherein when the lever portion is pressed, a moving distance of the lever portion and a moving distance of the movable part side lens pressing portion are equal.

4. The storage case having the soft intraocular lens folding function according to claim 1, wherein said base part and said movable part have soft intraocular lens supporting pins, when the lever portion is not pressed, the soft intraocular lens supporting pins support the soft intraocular lens, when the lever portion is pressed, the base part side soft intraocular lens supporting pin is stored in the movable part side lens pressing portion and the movable part side soft intraocular lens supporting pin is stored in the base part side lens pressing portion.

5. The storage case having the soft intraocular lens folding function according to claim 1, wherein in the base part side lens pressing portion and the movable part side lens pressing portion, portions which hold the soft intraocular lens are overhung relative to planes formed by the base part side holding portion and the movable part side holding portion.

6. The storage case having the soft intraocular lens folding function according to claim 1, wherein in the base part side lens pressing portion and the movable part side lens pressing portion, extractor guides are provided at surfaces with which an extractor is in contact when the folded soft intraocular lens is picked with the extractor.

7. The storage case having the soft intraocular lens folding function according to claim 1, wherein said base part and said lid part are provided with a light through-hole, which is used for performing inspection and/or measurement of the soft intraocular lens by emitting light to the soft intraocular lens from an outside of said storage case in a state in which said lid part protects the soft intraocular lens and said movable part by being fitted into said base part.

8. The storage case having the soft intraocular lens folding function according to claim 1, further comprising a control part which controls turning of the soft intraocular lens.

9. The storage case having the soft intraocular lens folding function according to claim 8, wherein said control part comprises columnar projections provided at said base part and controls movement of arm-shaped supporting portions provided at the soft intraocular lens.

* * * * *